United States Patent [19]

Wahlstrand et al.

[11] Patent Number: 5,438,990
[45] Date of Patent: Aug. 8, 1995

[54] MAGNETIC FIELD SENSOR

[75] Inventors: John D. Wahlstrand, Shoreview; David L. Thompson, Fridley, both of Minn.; Gary E. Nelson, Balsam Lake, Wis.

[73] Assignee: Medtronic, Inc., Minneapolis, Minn.

[21] Appl. No.: 150,746

[22] Filed: Nov. 12, 1993

Related U.S. Application Data

[63] Continuation of Ser. No. 982,132, Nov. 24, 1992, abandoned, which is a continuation-in-part of Ser. No. 750,143, Aug. 26, 1991, abandoned.

[51] Int. Cl.⁶ .............................................. A61B 5/05
[52] U.S. Cl. .............................. 128/653.1; 324/207.16
[58] Field of Search ................... 607/9, 22, 28, 32, 34, 607/60; 128/653.1; 3224/207.13, 207.16, 207.18, 207.2, 234, 235, 251, 252, 260; 257/421, 423, 426

[56] References Cited

U.S. PATENT DOCUMENTS

| | | | |
|---|---|---|---|
| 3,311,111 | 3/1967 | Bowers | 607/30 |
| 3,714,523 | 1/1973 | Bate | 257/426 |
| 3,714,559 | 1/1973 | Bate | 257/421 |
| 3,766,928 | 10/1973 | Goldberg et al. | 128/419 P |
| 3,777,762 | 12/1973 | Nielsen | 607/28 |
| 3,805,769 | 4/1974 | Sessions | 128/2.06 E |
| 3,920,005 | 11/1975 | Gombrich | 128/2.06 R |
| 3,945,387 | 3/1976 | Adams | 607/31 |
| 4,120,306 | 10/1978 | Renirk | 607/34 |
| 4,402,322 | 9/1983 | Duggan | 607/9 |
| 4,585,006 | 4/1986 | Livingston et al. | 607/28 |
| 4,739,264 | 4/1988 | Kamiya et al. | 324/251 |
| 4,908,527 | 3/1990 | Van Antwerp | 257/423 |
| 4,968,953 | 11/1990 | Kanda et al. | 324/207.16 |
| 5,073,858 | 12/1991 | Mills | 128/653.1 |
| 5,113,862 | 5/1992 | Morazaud | 607/22 |

Primary Examiner—William E. Kamm
Attorney, Agent, or Firm—Harold R. Patton

[57] ABSTRACT

An implantable medical device uses a solid-state sensor for detecting the application of an external magnetic field. The sensor includes first and second split-drain field-effect transistors (MAGFETs) which are cross-coupled such that an external magnetic field perpendicular to the channel regions of the MAGFETs causes an increase in current through one split-drain half of each MAGFET, and a decrease in current through the other split-drain half of each MAGFET. The sensor also includes a high-gain differential amplifier coupled between the MAGFETs for detecting changes in the current conducted through the respective split-drain halves, and produces an output voltage which changes upon application of an external magnetic field to the implantable medical device. The magnetic sensor operates at low power supply voltages and bias currents available in implantable medical devices such as a cardiac pacemaker, so that current drain and power consumption are minimized.

11 Claims, 14 Drawing Sheets

MAGNETIC FIELD SENSOR

This Application is a Continuation of U.S. Patent Application Ser. No. 07/982,132, filed Nov. 24, 1992, now abandoned, which was a Continuation-in-part of U.S. Patent Application Ser. No. 07/750,143, filed Aug. 26, 1991, now abandoned.

FIELD OF THE INVENTION

This invention relates generally to the field of implantable medical devices, and more particularly to an implantable medical device which uses a magnetic field sensor for detecting the application of a magnetic field to the medical device.

BACKGROUND OF THE INVENTION

In the field of medical devices which are implanted within the body of a human patient, such as implantable cardiac stimulators and the like, it is often desirable that certain operational parameters of the device be altered in a non-invasive (i.e. non-surgical) means. Various means of non-invasive communication with implanted devices have been previously disclosed. Since the introduction of demand cardiac pacemakers, one of the most common methods of non-invasive alteration of operational parameters employs a magnetically actuated reed switch contained within the implanted devices. The magnetic reed switch consists of a hermetically sealed cylindrical encapsulation housing two metallic reeds. The metallic reeds are disposed within the encapsulation such that when a sufficiently strong magnetic force is applied to the implanted device from outside the patient's body, the magnetic force draws the two reeds into electrical contact with one another, thereby completing an electrical circuit. When the magnetic field is withdrawn, the reeds separate, breaking the electrical circuit. Such an arrangement is disclosed, for example, in U.S. Pat. No. 3,805,796 entitled "Implantable Cardiac Pacer Having Adjustable Parameters" issued to Terry, Jr. et al. on Apr. 23, 1974, U.S. Pat. No. 3,920,005, entitled "Evaluation System for Cardiac Stimulators" issued to Gombrich et al. on Nov. 18, 1975, and U.S. Pat. No. 4,066,086 entitled "Programmable Body Stimulator" issued to Alferness et al. on Jan. 3, 1978, each assigned to the assignee of the present invention.

Reed switch closure is used to enable asynchronous operation for follow-up and trans-telephonic evaluation of the implanted pacemaker. In addition, rate and mode changes which occur upon reed switch closure are used to indicate device function and battery status. More recently, external devices have been developed which communicate with implanted devices via radio-frequency (RF) telemetry. An RF telemetry link allows two-way communication between an external device and an implanted device, and enables a wider range of operational parameters to be externally programmed. However, the use of an RF link does not necessarily eliminate the need for a magnetically-actuated reed switch. In U.S. Pat. No. 4,250,833 entitled "Digital Cardiac Pacemaker With Refractory, Reversion and Sense Reset Means" issued to David L. Thompson on Feb. 17, 1981, for example, the disclosed pacemaker cannot receive and process external RF telemetry signals until the reed switch is closed. Such an arrangement ensures that the implanted device will not be unintentionally re-programmed by extraneous RF signals to which the patient may be exposed.

Although magnetic reed switches are commonly employed in implanted devices, there are nonetheless several known problems associated with them. Reed switches are typically the only mechanical devices with moving parts in a pacemaker, making them more susceptible than the pacemaker's electronic components to damage or mechanical failure such as might result from vibration or mechanical shock. Although the glass encapsulation affords some measure of protection to the reeds, the capsule itself is susceptible to breakage. Furthermore, advances in electronic technology have resulted in progressively smaller pacemakers, so that the reed switch itself must be made very small, thereby adding to its fragility. Also, thin pacemakers, typically on the order of six to eight millimeters thick, prevent reed switches from being oriented in a preferred orthogonal orientation to the large flat surface area of the pacemaker case. Failure of the reed switch is particularly undesirable in the context of implantable devices, since replacement of such devices involves a surgical procedure.

While a reed switch must be sensitive enough to be responsive to an externally applied magnetic field, it is important that the switch not be so sensitive that it is responsive to every magnetic field to which the patient may be exposed in daily activity. As a result, the manufacturing tolerances for reed switches are low, making manufacturing costs high.

One attempt to overcome the disadvantages of a reed switch has been described in U.S. Pat. No. 3,766,928 issued to Goldberg et al. This patent discloses a potentiometer which is affixed to a small diametrically magnetized disc magnet. A second magnet is rotated outside the patient to cause the disc magnet to rotate and turn the potentiometer. This method itself has numerous disadvantages including the fact that it is also mechanical, and very small, and thus prone to breakage. In addition, the manipulation of the second magnet in order to adjust the potentiometer is more difficult and complex than the manipulation of the magnet required to actuate a reed switch.

Another attempt to overcome the disadvantages of a reed switch has been described in U.S. Pat. No. 4,301,804 entitled "Pacemaker With Hall Effect Externally Controlled Switch" issued on Nov. 24, 1981 to Thompson et al. and assigned to the assignee of the present invention. This patent discloses a pacemaker in which a circuit produces a strobe signal which is used to turn on a current flow through a Hall effect element once each pacemaker pulse cycle for a selected period of time. The presence of an external magnetic field alters the electrical properties of the Hall effect element (typically implemented in a bipolar integrated circuit fabrication process), so that a positive voltage is provided to the pacemaker circuitry when the element is strobed. While the Hall effect element is not a mechanical device, and is in that respect preferable to a reed'-switch, the Hall effect element has proven to be less sensitive than a reed switch, requires expensive processing and packaging, and is not compatible with standard linear CMOS processing which is preferentially used in implantable medical devices.

As an alternative to using mechanical reed-switches or Hall effect elements to detect and measure magnetic fields, it has been proposed in the prior art to employ split-drain field-effect transistors, sometimes called MAGFETs, for this purpose. Although similar to a conventional field-effect transistor (FET), the drain of a MAGFET is split into two isolated halves. Application of a magnetic field to a MAGFET device gives rise to a differential in the currents in the two split-drain-halves, the extent of this differential being directly proportional to the strength of the applied magnetic field. Although MAGFETs, like Hall-effect devices, have the advantage of being solid-state devices, some problems with prior MAGFETs are known. One problem relates to the sensitivity of these devices to magnetic fields. Typically, the gain constant of a MAGFET is small, i.e. the current differential between the drain current in respective drain-halves is rather slight for a given change in magnetic field intensity. In order for a MAGFET to be readily utilized to detect and measure an external magnetic field, it is desirable to maximize the gain constant of the MAGFET. It is has been taught in the prior art that the gain constant of a MAGFET can be increased by raising the bias current of the MAGFET in steady-state. (See, e.g., Misra et al., "A Novel High Gain MOS Magnetic Field Sensor", *Sensors and Actuators*, pp. 213–221 (1986)). In addition, many prior art references discuss operation of MAGFETs with five- to ten-volt power supplies and 10- to 620-micro-amp bias currents. (See, e.g., Misra, "A Novel CMOS Magnetic Field Sensor Array", *IEEE Journal of Solid-State Circuits*, v. 25, no. 2, April 1990, pp. 623–625; Nathan et al., "Design of a CMOS Oscillator with Magnetic-Field Frequency Modulation", *IEEE Journal of Solid-State Circuits*, v. SC-22, n. 2, April 1987, pp. 230–232.) Such power supply voltages and bias currents are not available in implantable pacemakers, however, which must operate with one- to three-volt power supplies and ten to one-hundred nano-amp bias currents.

Another method of the prior art for achieving increased sensitivity to magnetic fields involves using an array of MAGFET devices in a tree arrangement, and combining the drain-halves from the individual MAGFETs such that the effect of the magnetic field is measured by the additive effect of the current differential in each of the individual split-drain pairs. (See, e.g., Misra et al., "A Novel High Gain MOS Magnetic Field Sensor", *Sensors and Actuators*, pp. 213–221 (1986).) This solution, however, requires a higher-level supply voltage, since the threshold voltages of MAGFETs coupled in this manner are additive. Moreover, the use of multiple MAGFET devices results in a corresponding increase in total circuit area, and an increase in current drain for the sensor. Thus, prior art techniques for increasing the gain constant of MAGFET devices have proven unsuitable for application in implantable medical devices, which must maintain small size, long-term stability and reliability, minimal power-supply voltage levels and minimal current drain.

It is accordingly a feature of the present invention that an implantable medical device is provided Which uses a non-mechanical sensor which is sufficiently sensitive to external magnetic fields.

It is another feature of the present invention that an implantable medical device using a magnetic sensor is operable at the low supply voltages and bias currents available in an implanted medical device.

It is still another feature of the present invention that an implantable medical device uses a magnetically-actuated device which is simple to produce using conventional CMOS processing techniques.

It is yet another feature of the present invention that an implantable medical device using a magnetically actuated sensor is sufficiently sensitive to external magnetic fields even when the sensor is provided with the low supply voltages and bias currents of an implantable medical device.

SUMMARY OF THE INVENTION

The foregoing and other features of the present invention are realized in an implantable medical device which uses a CMOS sensor comprising a cross-coupled arrangement of two split-drain field-effect transistors (MAGFETs). In the absence of an external magnetic field, the total drain current in each MAGFET is evenly divided between each half of the split-drain in that MAGFET. An external magnetic field directed perpendicularly to the plane of the channel in each MAGFET gives rise to a Lorentz force exerted on injected carriers in the MAGFET, causing a variation in the drain current in each half of the split-drain. Since the total drain current in each MAGFET remains the same, an increase in the drain current in one half of a MAGFET's split-drain will be accompanied by a corresponding decrease in the drain current in the other half of the split-drain. In this way, the presence and strength of an external magnetic field is manifested as a voltage or current differential between the two halves of the split-drain in each MAGFET. A high-gain differential amplifier situated between the cross-coupled MAGFETS can therefore produce an output indicative of the application of an external magnetic field.

In accordance with one embodiment of the invention, an implantable cardiac pacemaker uses a CMOS magnetic field sensor with cross-coupling of split-drain field-effect transistors resulting in a doubling of the voltage differential from application of a given magnetic field. The enhanced voltage differential and low current drain of the sensor makes the implanted pacemaker sufficiently sensitive to external magnetic fields.

BRIEF DESCRIPTION OF THE DRAWINGS

The novel features and advantages believed characteristic of the present invention are set forth in the appended claims. The invention itself, however, as well as other features and advantages thereof, will be best understood by reference to a detailed description of a specific embodiment of the present invention which follows, when read in conjunction with the accompanying drawings, wherein:

DETAILED DESCRIPTION OF A SPECIFIC EMBODIMENT OF THE INVENTION

Figure 1:
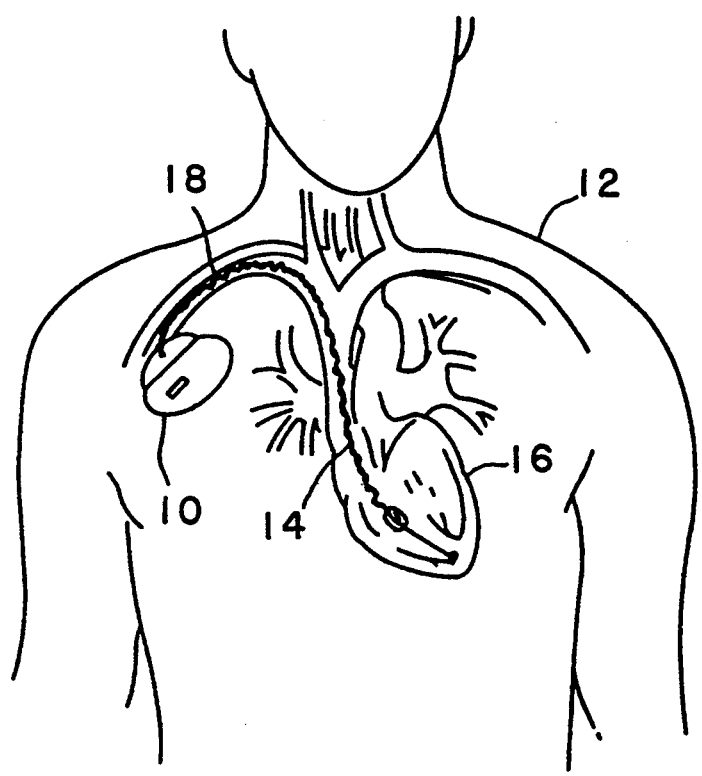
FIG. 1 is a diagram showing the placement in a patient of a pacemaker in accordance with one embodiment of the present invention.

FIG. 1 shows generally how a pacemaker 10 in accordance with the present invention may be implanted in a patient 12. A pacemaker lead 14 is electrically coupled to pacemaker 10 and extends into the patient's heart 16 via a vein 18. The distal end of lead 14 includes one or more exposed conductive electrodes for receiving electrical cardiac signals and for delivering electrical pacing stimuli to the patient's heart 16.

Figure 2:
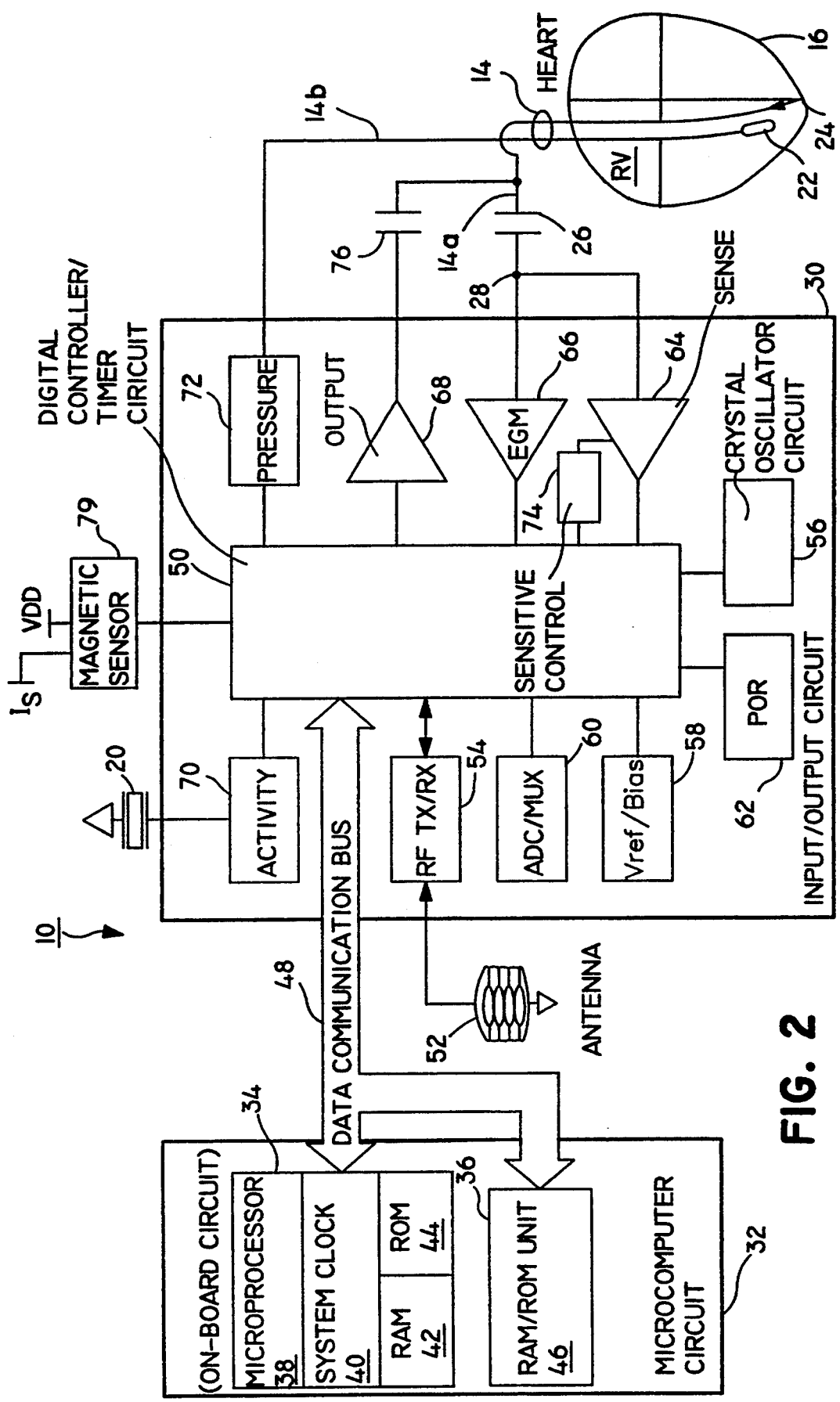
FIG. 2 is a block diagram of the circuitry of the pacemaker of FIG. 1.

Turning to FIG. 2, a block diagram of pacemaker 10 from FIG. 1 is shown. Although the present invention is described in conjunction with a pacemaker 10 having a microprocessor-based architecture, it will be understood that it could be implemented in a digital logic based, custom integrated circuit architecture, if desired. It will also be understood that the present invention may be utilized in conjunction with other implantable medical devices, such as cardioverters, defibrillators, neural stimulators, and the like.

Figure 6:
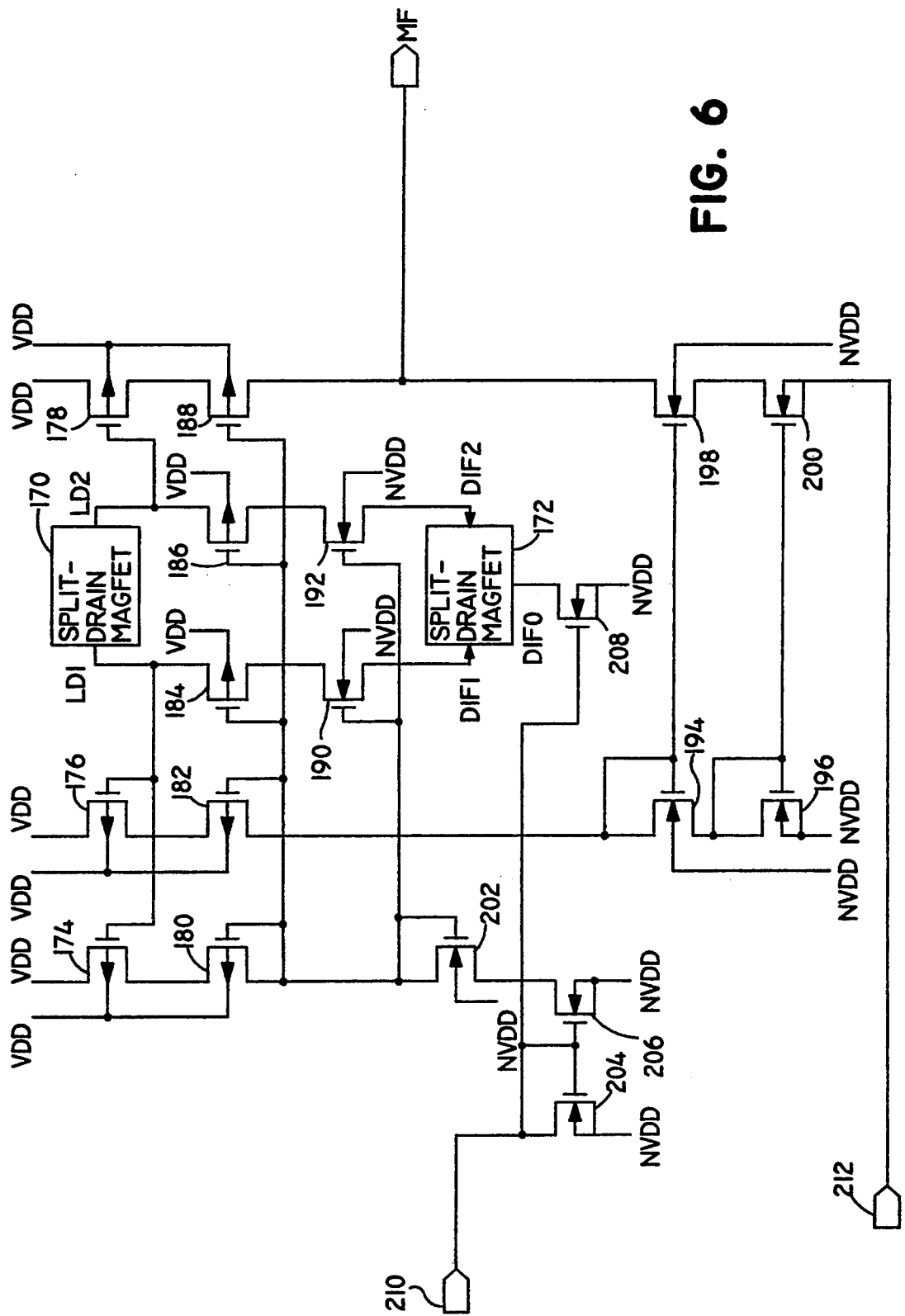
FIG. 6 is a schematic diagram of a magnetic sensor circuit suitable for use in the pacemaker of FIG. 1.

In the embodiment shown in FIG. 1, pacemaker 10 includes a magnetic sensor 79, which may be, for example, a very high gain differential amplifier coupled between the cross-coupled drains of two split-drain MAGFET's as represented in FIG. 6. Sensor 79 provides an output indicative of the application of an external magnetic field. In addition, pacemaker 10 may include an activity sensor 20 and a pressure sensor 22. Sensor 20 may be, for example, a piezoelectric element bonded to the inside of the pacemaker's 10 housing where the sensor provides an output which varies as a function of a measured parameter that relates to the metabolic requirements of patient 12. Sensor 22 may be a piezoelectric element, which may be similarly be used to ascertain the metabolic requirements and/or cardiac output of patient 12.

Pacemaker 10 is schematically shown in FIG. 2 to be electrically coupled via a pacing lead 14 to a patient's heart 16. Lead 14 includes an intracardiac electrode 24 and pressure sensor 22 located near its distal end and positioned within the right ventricular chamber of heart 16. Lead 14 can carry either unipolar or bipolar electrodes as is well known in the art. Electrode 24 is coupled via suitable lead conductor 14a through input capacitor 26 to node 28 and to input terminals of an input-/output circuit 30. Output from magnetic sensor 79 is coupled to input/output circuit 30. Output from sensor 20 is also coupled to input/output circuit 30 and output from pressure sensor 22 is coupled to input/output circuit 30 via suitable lead conductor 14b.

Input/output circuit 30 contains the operating input and output analog circuits for digital controlling and timing circuits necessary for the detection of electrical signals derived from heart 16, such as the cardiac electrogram, output from sensor 20, output from sensor 22 and the output from magnetic sensor 79, as well as for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. Off-board circuit 36 includes an off-board RAM/ROM unit 46 which shall be hereinafter described in greater detail. Microcomputer circuit 32 is coupled by data communication bus 48 to a digital controller/timer circuit 50. Microcomputer circuit 32 may be fabricated of custom integrated circuit devices augmented by standard RAM/ROM components.

It will be understood that the electrical components represented in FIG. 2 are powered by an appropriate implantable battery power source, not shown, in accordance with common practice in the art.

An antenna 52 is connected to input/output circuit 30 for purposes of uplink/downlink telemetry through RF transmitter/receiver (RF TX/RX) unit 54. Telemetering both analog and digital data between antenna 52 and an external device, such as an external programer (not shown), is accomplished in the presently disclosed embodiment by means of all data first being digitally encoded and then pulse-position modulated on a damped RF carrier, as substantially described in U.S. Pat. No. 5,127,404, issued Jul. 7, 1992, entitled "Improved Telemetry Format", which is assigned to the assignee of the present invention and which is incorporated herein by reference.

A crystal oscillator circuit 56, typically a 32,768 Hz crystal-controlled oscillator, provides main timing clock signals to digital controller/timer circuit 50. A Vref/Bias circuit 58 generates stable voltage reference and bias currents for the analog circuits of input/output circuit 30. An analog-to-digital converter/multiplexer (ADC/MUX) unit 60 digitizes analog signals and voltages to provide telemetry and battery end-of-life (EOL) replacement function. A power-on-reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input-/output circuit 30.

Digital controller/timer circuit 50 is coupled to a sense amplifier 64 and an electrogram amplifier 66 for receiving amplified and processed signals picked up from electrode 24 through lead conductor 14a and capacitor 26 representative of the electrical activity of the patient/s heart 16. Sense amplifier 64 produces a sensed event signal for resetting the escape interval timer within circuit 50. The electrogram signal developed by EGM amplifier 66 is used in those occasions when the implanted device is being interrogated by an external programmer, not shown, in order to transmit by uplink telemetry a representation of the analog electrogram of the patient's electrical heart activity as described in U.S. Pat. No. 4,556,063, issued to Thompson et al., assigned to the assignee of the present invention and incorporated herein by reference. An output pulse generator 68 provides the pacing stimulus to the patient's heart 16 via output capacitor 76 in response to a pacing trigger signal developed by digital controller/timer circuit 50 each time the escape interval times out, or an externally transmitted pacing command has been received, or in response to other stored commands as is well known in the pacing art.

Digital controller/timer circuit 50 is coupled to an activity circuit 70 for receiving, processing, and amplifying signals received from activity sensor 20. Activity circuit 70 produces an activity signal which is representative of the patient's metabolic requirements. Similarly, digital controller/timer circuit 50 is coupled to a pressure circuit 72 for receiving, amplifying and processing sensor output from pressure sensor 22. In the presently disclosed embodiment of the invention, pressure circuit 72 produces a pressure signal which is asserted only when the sensor output from pressure sensor 22 indicates that pressure in the patient's right ventricle has exceeded a predetermined pressure threshold value. When the pressure exceeds the pressure threshold value, this is called a "true" pressure beat, and causes pressure circuit 72 to assert the pressure signal received by digital controller/timer circuit 50. Pressures which do not exceed this value are called "false" pressure beats, and do not lead to assertion of the pressure signal.

Figure 3A:
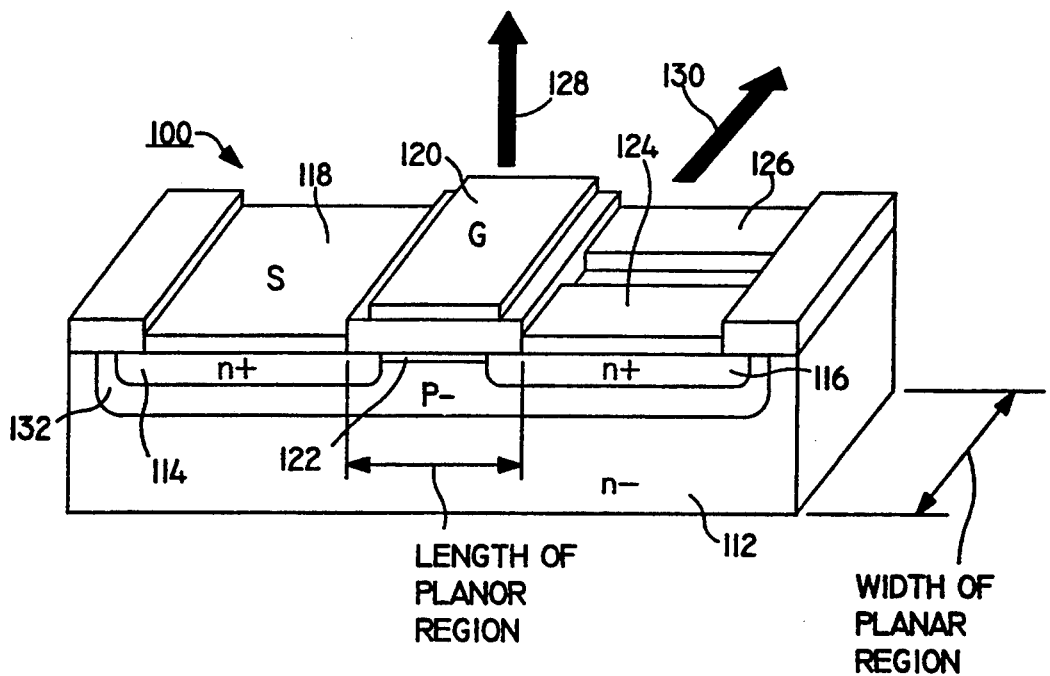
FIGS. 3*a* and 3*b* are perspective views of split-drain FETs utilized in a magnetic sensor suitable for use in the pacemaker of FIG. 1.
Figure 3B:
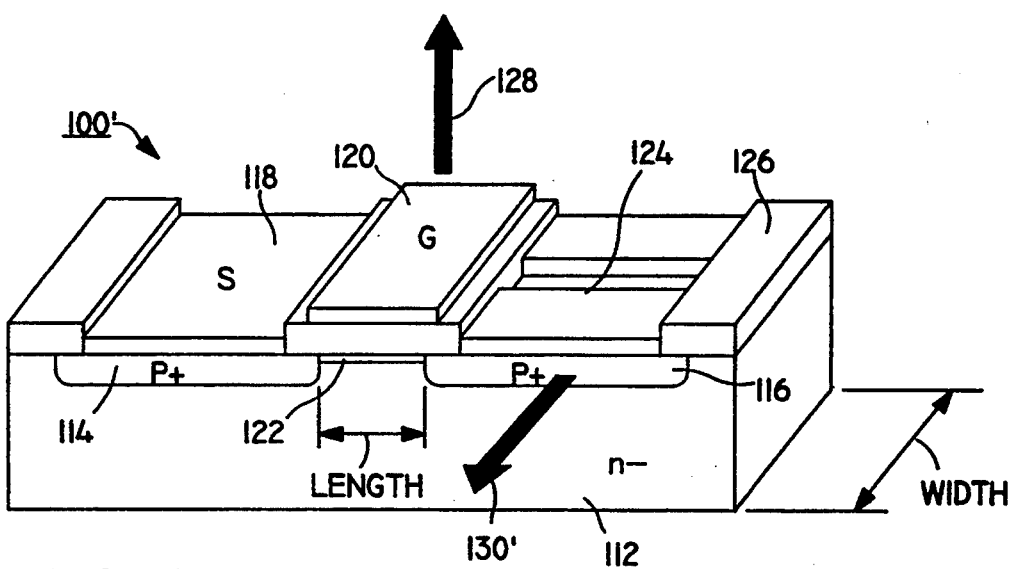

In accordance with the present invention, digital controller/timer circuit 50 is coupled to a magnetic sensor 79 for receiving and processing signals received from magnetic sensor 79 resulting from application of a magnetic field 128 as illustrated in FIGS. 3a and 3b. A magnetic sensor 79 suitable for use in the pacemaker circuit illustrated in FIG. 2 will be described hereinafter with reference to FIGS. 3 through 14.

Referring now to FIG. 3a, a three-dimensional view of an N-channel split-drain MAGFET 100 is shown. As in conventional N-channel FETs, split-drain MAGFET 100 comprises an N-type substrate 112 having a P-well 132 formed therein. P-well 132, in turn, has N-type source and drain regions 114 and 116, respectively, formed therein. The metal source 118 and gate 120 are also conventional FET structures. Gate 120 covers a channel region 122 disposed between source region 114 and drain region 116. Unlike a conventional FET, however, the metal drain of MAGFET 100 is split into two distinct halves, 124 and 126, which are electrically isolated from one another. FIG. 3b is a three-dimensional view of a similar P-channel Split-drain MAGFET 100' in which components identical to those of FIG. 3a have retained identical reference numerals. MAGFET 100' differs from MAGFET 100 only in the wafer processing steps and the absence of a P-well 132.

As would be appreciated by one of ordinary skill in the semiconductor art, if a magnetic field is applied to MAGFET 100 in the direction indicated by arrow 128, perpendicular to the plane of channel region 122, a Lorentz force is exerted on injected carriers. The direction of the Lorentz force can be determined using the so-called "right-hand rule": if the thumb of a person's right hand is pointed in the direction of the magnetic field, the Lorentz force resulting from that magnetic field will be exerted in the direction of the curled fingers of that person's right hand. In FET 100 of FIG. 3a, therefore, a magnetic field in the direction of arrow 128 will give rise to a Lorentz force directed in the direction indicated by arrow 130, perpendicular to arrow 128 and in the perpendicular direction between split-drain-half 124 and split-drain-half 126. In FET 100' of FIG. 3b, a magnetic field in the direction of arrow 128 will give rise to a Lorentz force directed in the direction indicated by arrow 130', perpendicular to arrow 128, in the perpendicular direction between split-drain half 124 and split-drain half 126, and in the opposite direction from arrow 130 in FIG. 3a. The opposing directions of arrows 130 and 130' of FIGS. 3a and 3b is due to electrons and holes being the predominant carriers in FIG. 100 and 100' respectively As a result of this Lorentz force, the drain current of MAGFET 100, which is, as noted above, normally evenly divided between the split-drain-halves 124 and 126, will be concentrated more in the split drain half 126 and less in split drain half 124. In particular, if MAGFET 100 is biased such that a total drain current $I_T$-amps flows through drains-halves 124 and 126, in the absence of an external magnetic field a current of $\frac{1}{2}I_T$-amps will flow in drain-half 124, and $\frac{1}{2}I_T$-amps in drain-half 126. When an external magnetic field is applied, the total drain current $I_T$-amps remains the same, but some amount $(\frac{1}{2}I_T+i)$-amps will flow in drain-half 126, while some amount $(\frac{1}{2}I_T-i)$-amps will flow in drain-half 124. This results in a difference of 2i-amps between the current in drain-halves 124 and 126; a measurement of the 2i-amp difference between the currents in the respective drain-halves 124 and 126 can thus be used to determine the presence and strength of an external magnetic field.

Figure 4A:
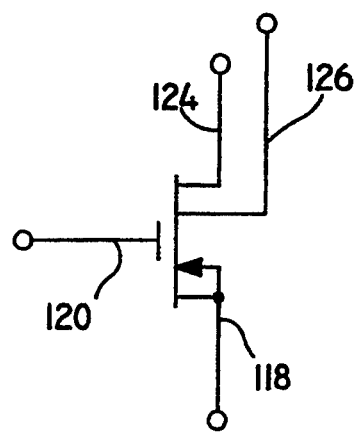
FIGS. 4*a* and 4*b* are alternative schematic representations of the split-drain FET of FIG. 3 suitable for use in the pacemaker of FIG. 1.
Figure 4B:
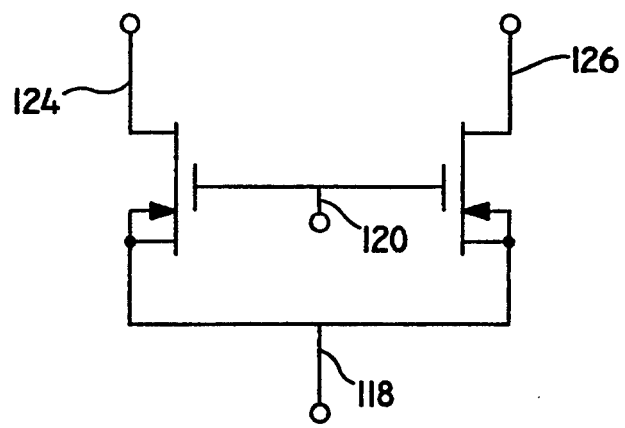

A circuit symbol used to schematically represent a MAGFET 100 is shown in FIG. 4a. An alternative schematic representation of MAGFET 100 is shown in FIG. 4b. In the representations of FIGS. 4a and 4b, as in FIG. 3, reference numeral 118 denotes the source terminal of MAGFET 100, reference numeral 120 denotes the gate terminal, and reference numerals 124 and 126 denote the two split-drain halves.

Figure 5:
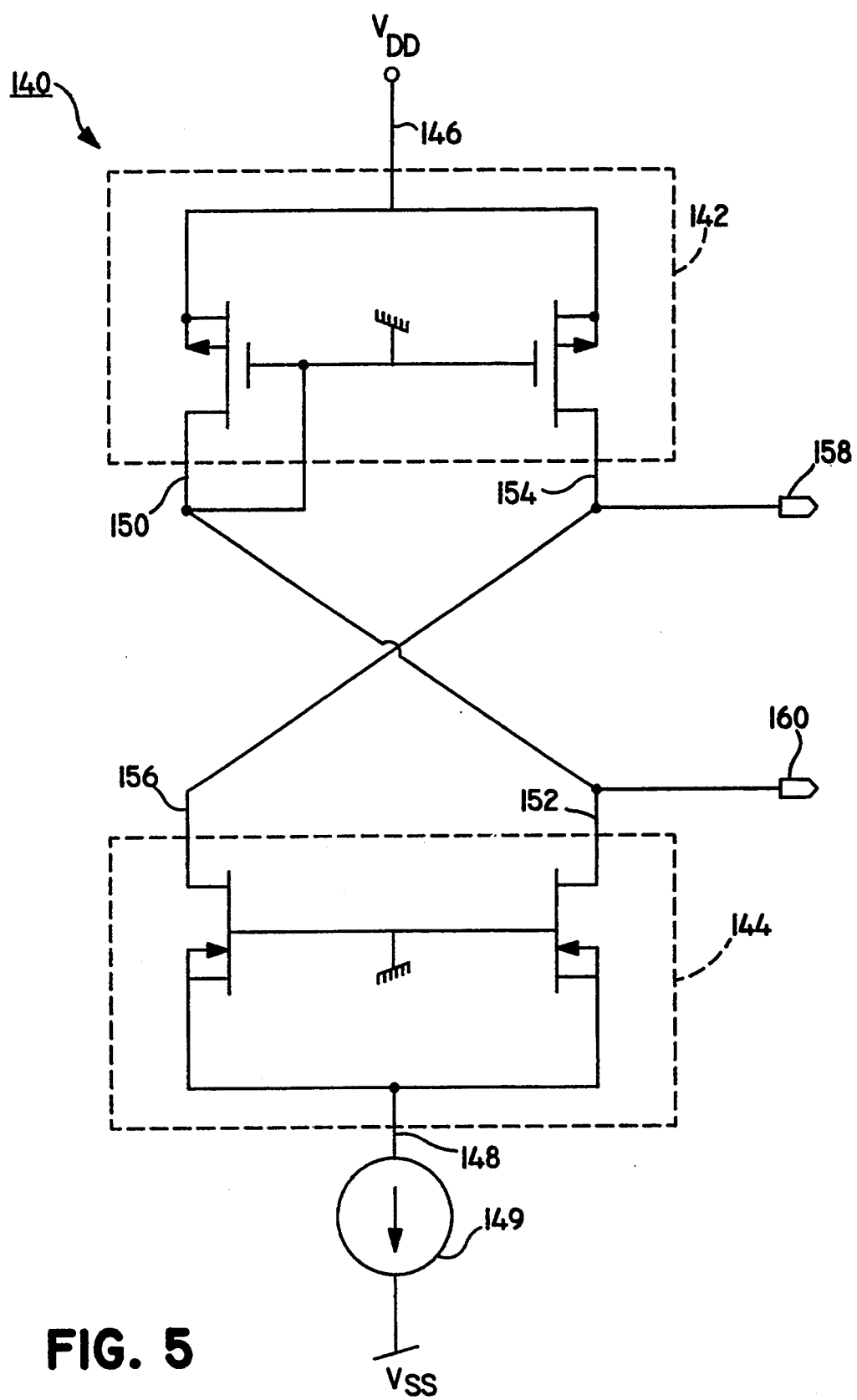
FIG. 5 is a schematic diagram illustrating the cross-coupling of split-drain FET's in a magnetic sensor suitable for use in the pacemaker of FIG. 1.

Turning now to FIG. 5, a magnetic sensor 140 in accordance with one embodiment of the present invention is shown in schematic form, wherein two MAGFETS 142 and 144 are represented using the convention of FIG. 4b. Sensor 140 consists of a P-channel MAGFET indicated by dashed line 142, and an N-channel MAGFET indicated by dashed line 144. Source terminal 146 of MAGFET 42 receives a power supply voltage $V_{DD}$, provided, for example, from a battery. Source terminal 148 of MAGFET 144 is coupled to a regulated current source 149. The silicon substrate on which sensor 140 is constructed is coupled to a negative supply voltage $NV_{DD}$, which shall variously be referred to herein and in the Figures as $NV_{DD}$ or $V_{SS}$. Split-drain-half 150 of MAGFET 142 is coupled to split-drain-half 152 of MAGFET 144, while split-drain-half 154 of MAGFET 142 is coupled to split-drain-half 156 of MAGFET 144. A first output terminal 158 is coupled to the drain-halves 154 and 156, while a second output terminal 160 is coupled to the drain-halves 150 and 152.

MAGFET 142 functions in sensor 140 as an active load. In the absence of an external magnetic field, the currents in respective split-drain-halves 150 and 154 of MAGFET 142 are equal, so that the voltages on respective output terminals 158 and 160 are likewise equal, with a voltage level near the midpoint between $V_{DD}$ and $V_{SS}$. MAGFETs 142 and 144 are physically arranged relative to one another on the substrate such that an external magnetic field applied to sensor 140 will cause drain current in the respective MAGFETs 142 and 144 to be "crowded", by Lorentz force, either into split-drain-halves 150 and 156, or into split-drain-halves 152 and 154, depending upon the polarity of the magnetic field.

In the case that an applied magnetic field causes current to be increased in split-drain-halves 150 and 156, a corresponding reduction in the currents in split-drain-halves 152 and 154 will also occur. Since the current in split-drain-half 150 is increased, while the current in split-drain-half 152 is decreased, the voltage at output terminal 160 will tend to increase; conversely, since the current in split-drain-half 154 is decreased, while the current in split-drain-half 156 in increased, the voltage at output terminal 158 will tend to decrease.

In the case that an applied magnetic field causes current to increase in split-drain-halves 152 and 154, a corresponding reduction in the currents in split-drain-halves 150 and 156 will occur. In this case, the voltage at output terminal 158 increases, while the voltage at output terminal 160 decreases. As would be appreciated by one of ordinary skill in the design of electronic circuits, a differential amplifier situated between the two output terminals 158 and 160 can be used to detect changes in the relative voltages of output terminals 158 and 160, thereby providing an indication of an externally applied magnetic field.

Turning now to FIG. 6, a schematic diagram of a magnetic sensor suitable for use in the implantable pacemaker circuit illustrated in FIG. 2 is shown. The sensor of FIG. 6 is a very high gain differential amplifier which consists of MAGFET 172 as the input differential pair, transistors 190 and 192 as cascodes to the differential pair, MAGFET 170 as the active load for the differential amplifier, transistors 184 and 186 as cascodes to the active load, transistors 178, 188, 198 and 200 as the output stage of the differential amplifier (which produces an output voltage at the terminal designated MF), transistors 176, 182, 194 and 196 as the level shifter to drive the gates of transistors 198 and 200, and transistors 174, 180, 202, 206 and 204 as the biasing network for the differential amplifier. A current source is coupled to the sensor of FIG. 6 at terminal 210. The current source is applied to a current mirror comprising devices 204 and 206, and the regulated output current from the current mirror provides the proper current at the source terminal of MAGFET 172. Trimming of wafer process variations is accomplished via a resistor (not shown) between the $NV_{DD}$ power supply and terminal 212. The resistor is adjusted while the sensor of FIG. 6 is in a zero-intensity magnetic field.

Figure 7:
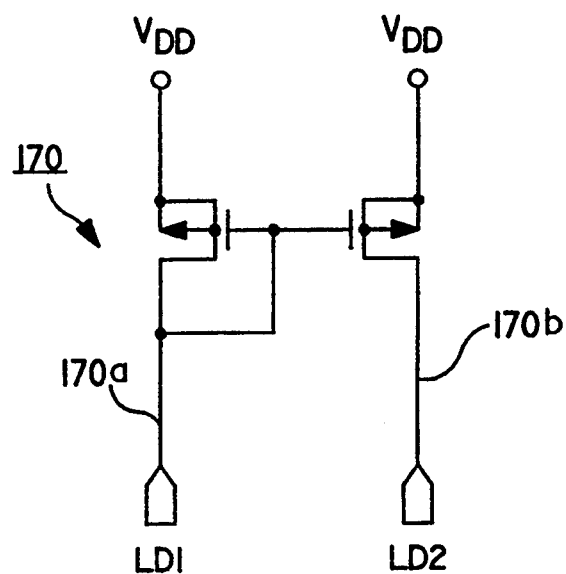
FIG. 7 is a schematic diagram of the P-channel MAGFET from the circuit of FIG. 6.

In FIG. 7, a schematic representation of MAGFET 170 is shown, using the representation of a split-drain transistor of FIG. 4b. In FIG. 7, one split-drain half of MAGFET 170 is designated as 170a, and the second split-drain half of MAGFET 170 is designated as 170b. MAGFET 170 is a P-channel device which serves as an active load device, in the same manner as MAGFET 142 served as the active load in the circuit of FIG. 5.

Figure 8:
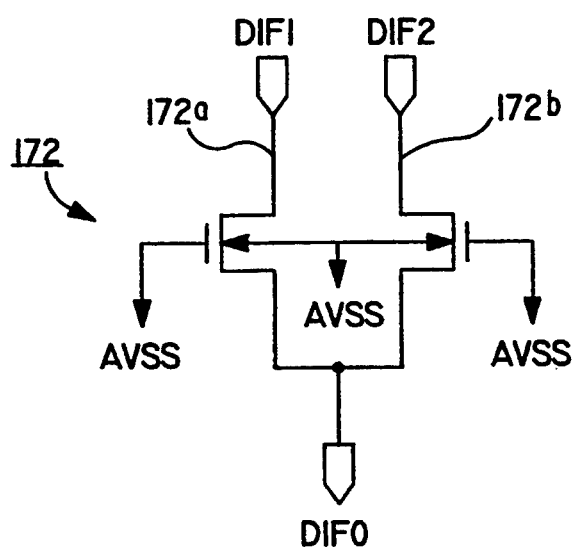
FIG. 8 is a schematic diagram of the N-channel MAGFET from the circuit of FIG. 6.

MAGFET 170 is coupled to the sensor of FIG. 6 via terminals designated LD1 and LD2. In FIG. 8, a schematic representation of MAGFET 172 is shown, also using the representation of a split-drain transistor of FIG. 4b. In FIG. 8, one split-drain half of MAGFET 172 is designated as 172a, and the other split-drain half of MAGFET 172 is designated as 172b. MAGFET 172 is an N-channel device which is coupled to the sensor of FIG. 6 via terminals DIF0, DIF1, and DIF2.

As can be seen in FIGS. 6, 7, and 8, split-drain half 170a of MAGFET 170 is coupled, via FETs 184 and 190, to split-drain half 172b of MAGFET 172. Similarly, split-drain half 170b of MAGFET 170 is coupled, via FETs 186 and 192, to split-drain half 172b of MAGFET 172. Subject, of course, to unavoidable CMOS process variation, the bias current through the split-drain halves 170a and 172a will be equal to the bias current through split-drain halves 170b and 172b. The differential amplifier comprising FETs 174–202 is biased such that in the absence of an external magnetic field, the voltage at the MF output terminal will be $V_{DD}$ (or $NV_{DD}$). Since the differential amplifier comprising FETs 174–202 has very high gain, the slight change in current through the split-drain halves resulting from the application of an external magnetic field causes the voltage at output terminal MF to change to $NV_{DD}$ (or $V_{DD}$).

As the sensor of FIG. 6 is part of the circuitry in an implantable pacemaker such as illustrated in FIG. 2, it is essential that sensor 140 operate with low current drain and minimal positive and negative voltage supply levels $V_{DD}$ and $NV_{DD}$. At the same time, it is desirable to ensure that the sensor of FIG. 6 remain very sensitive to external magnetic fields. As previously noted, numerous references in the prior art have taught that the sensitivity of MAGFET devices to magnetic fields may be enhanced by increasing the power supply levels and bias current of the devices. However, the Inventors have achieved sensitivities of 1200-volts/Tesla with the sensor of FIG. 6 operated with supply voltages of ±1.8 to ±3.0-volts and bias currents of ten to one-hundred nano-amps. This sensitivity is roughly one-thousand times previously published values. (See, e.g., Misra, et al. (1986)). The sensitivity of the sensor to external magnetic fields, the gain constant of the differential amplifier circuitry, and the current drain characteristics of the sensor of FIG. 6 are also affected by the sizes of the split-drain MAGFETs illustrated in FIG. 3a and 3b. A number of different combinations of MAGFET sizes are contemplated by the inventors. As would be appreciated by one of ordinary skill in the design of semiconductor circuits, the critical parameter of FET devices is the channel size, which may be designated as a ratio of channel width to channel length-(W/L). In Table 1, a listing of the MAGFET sizes of one implementation of the sensor of FIG. 6 is provided.

TABLE 1

| MAGFET | CHANNEL SIZE (width/length, in microns) |
| --- | --- |
| 170 | 316/316 |
| 172 | 316/316 |
| 174 | 38/4 |
| 176 | 38/4 |
| 178 | 38/4 |
| 180 | 38/4 |
| 182 | 38/4 |
| 184 | 38/4 |
| 186 | 38/4 |

TABLE 1-continued

| MAGFET | CHANNEL SIZE (width/length, in microns) |
|---|---|
| 188 | 38/4 |
| 190 | 15/4 |
| 192 | 15/4 |
| 194 | 15/4 |
| 196 | 15/4 |
| 198 | 60/12 |
| 200 | 60/12 |
| 202 | 15/4 |
| 204 | 2 × 60/12 |
| 206 | 60/12 |
| 208 | 2 × 60/12 |

Although the implementation of the sensor of FIG. 6 using MAGFET channel sizes from Table 1 is presently preferred by the inventors, two additional implementations are contemplated. The first of these alternative embodiments employs devices according to Table 1, except that MAGFET device 170 is replaced with a MAGFET device having a width-to-length (w/l) ratio of 316μ/5μ instead of 316μ/316μ. In the second alternative embodiment, MAGFET device 170 is replaced with a MAGFET device having a w/l ratio of 6μ/316μ.

Figure 9:
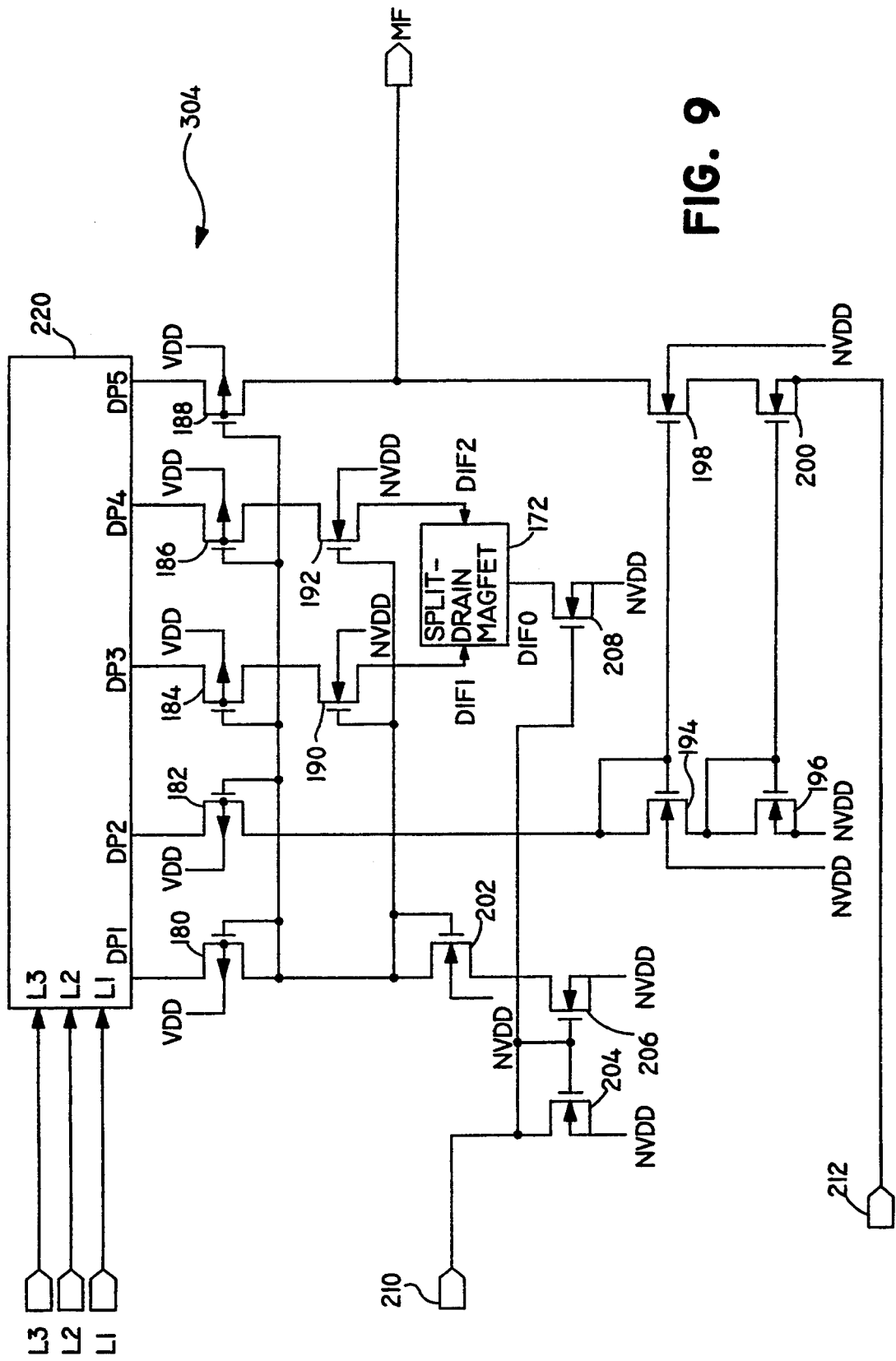
FIG. 9 is a schematic diagram of an alternative embodiment of a magnetic sensor circuit suitable for use in the pacemaker of FIG. 1.

While the implementation of the sensor of FIG. 6 using the MAGFET sizes of Table 1 is deemed by the inventors to be a preferred method of practicing the present invention, it may nonetheless be desirable, in a given application, to consider alternative implementations. To this end, the inventors have employed a multiplexing arrangement, such as is shown in FIG. 9, which allows for several alternative combinations of active loads to be introduced into a magnetic sensor 304 in accordance with the present invention. In FIG. 9, those devices which are identical to corresponding devices in the implementation of FIG. 6 have retained identical reference numerals. The implementation of FIG. 9, however, further includes a multiplexer 220, which is shown in greater detail in FIG. 10. Multiplexer 220 receives input signals L1, L2, and L3, which are used to select one of several active loads to be introduced into the magnetic sensor 304.

Figure 10:
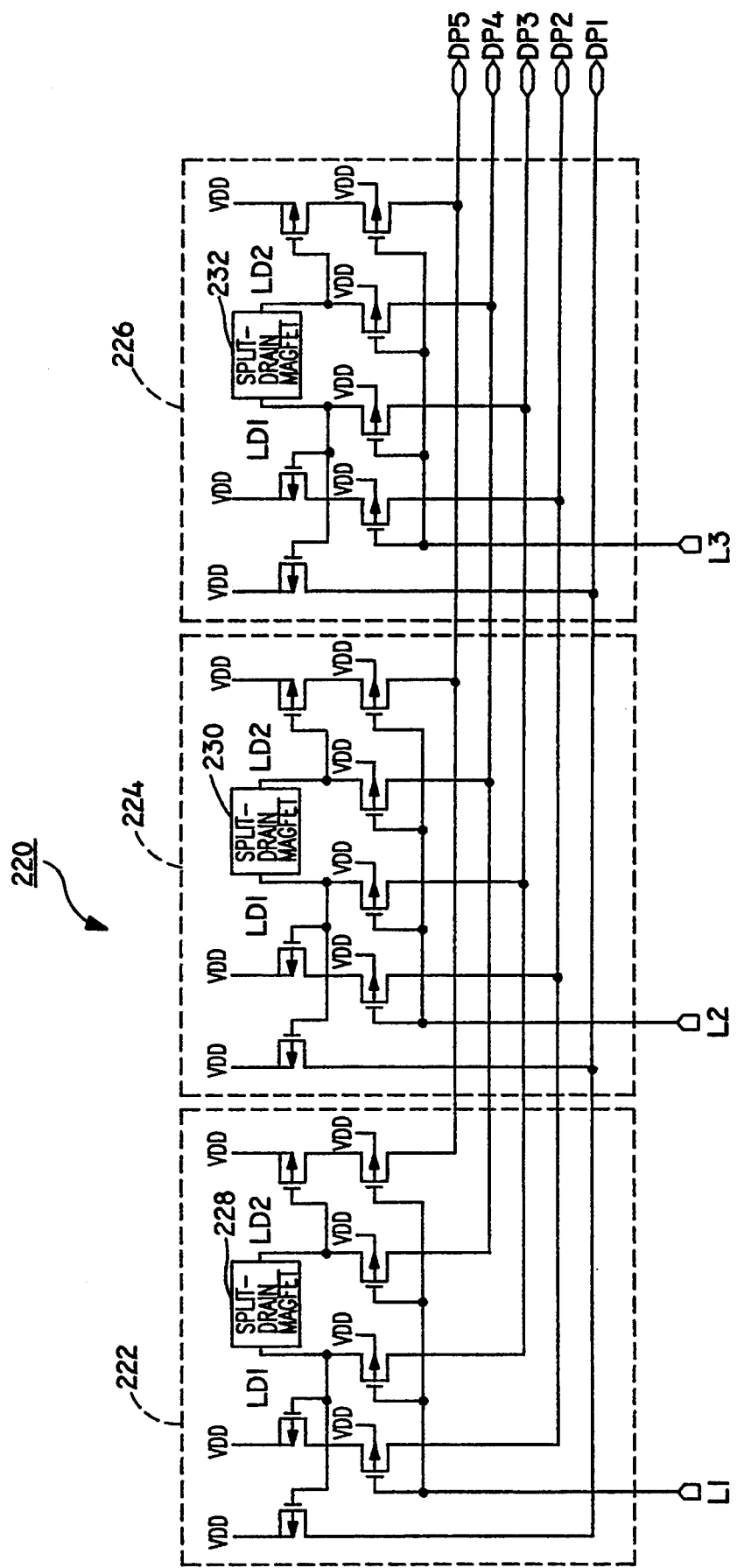
FIG. 10 is a schematic diagram of the multiplexer from the circuit of FIG. 9.

With reference to FIG. 10, each of the devices in multiplexer 220 has a w/l ratio of 38μ/4μ. Multiplexer circuitry 220 includes three separate active load portions, indicated in FIG. 10 by dashed lines 222, 224, and 226. Active load portion 222 includes a MAGFET device 228. Active load portion 124 includes a MAGFET device 230. Active load portion 226 includes a MAGFET device 232. As would be readily apparent to one of ordinary skill in the design of semiconductor circuits, applying a negative voltage on either line L1, L2, or L3, with all others held high, causes active load portion 222, 224, or 226, respectively, to be applied to the circuitry of FIG. 9 via terminals DP1, DP2, DP3, DP4, and DP5. Thus, by selecting either L1, L2, or L3, MAGFET 228, 230, or 232, respectively, is introduced into the magnetic sensor 304 of FIG. 9. In this way, various active load devices can be compared and tested for their suitability in a given application of the present invention, or, alternatively, a programmable sensitivity may be employed to allow a variable level of magnetic field intensity control.

The ability to program the sensitivity of the MAGFET will allow the use of varying levels of access to programming and diagnostic capabilities of implantable medical devices where the magnetic switch function is an interlock to initiate programming and telemetry. For example, company representatives aiding in the troubleshooting of a problem implant could have access to additional programmable parameters or device self-check routines, functions to which clinicians would be prevented access by means of a higher magnetic threshold. Additionally, patients with implanted neurostimulators are typically sent home with a patient programmer which enables the device's standard programming link but, via software, limits programmability. Undesirable programming could occur with the standard link being enabled. A programmable higher magnetic threshold can be used to allow very limited access to programmable parameters by a patient.

Figure 11:
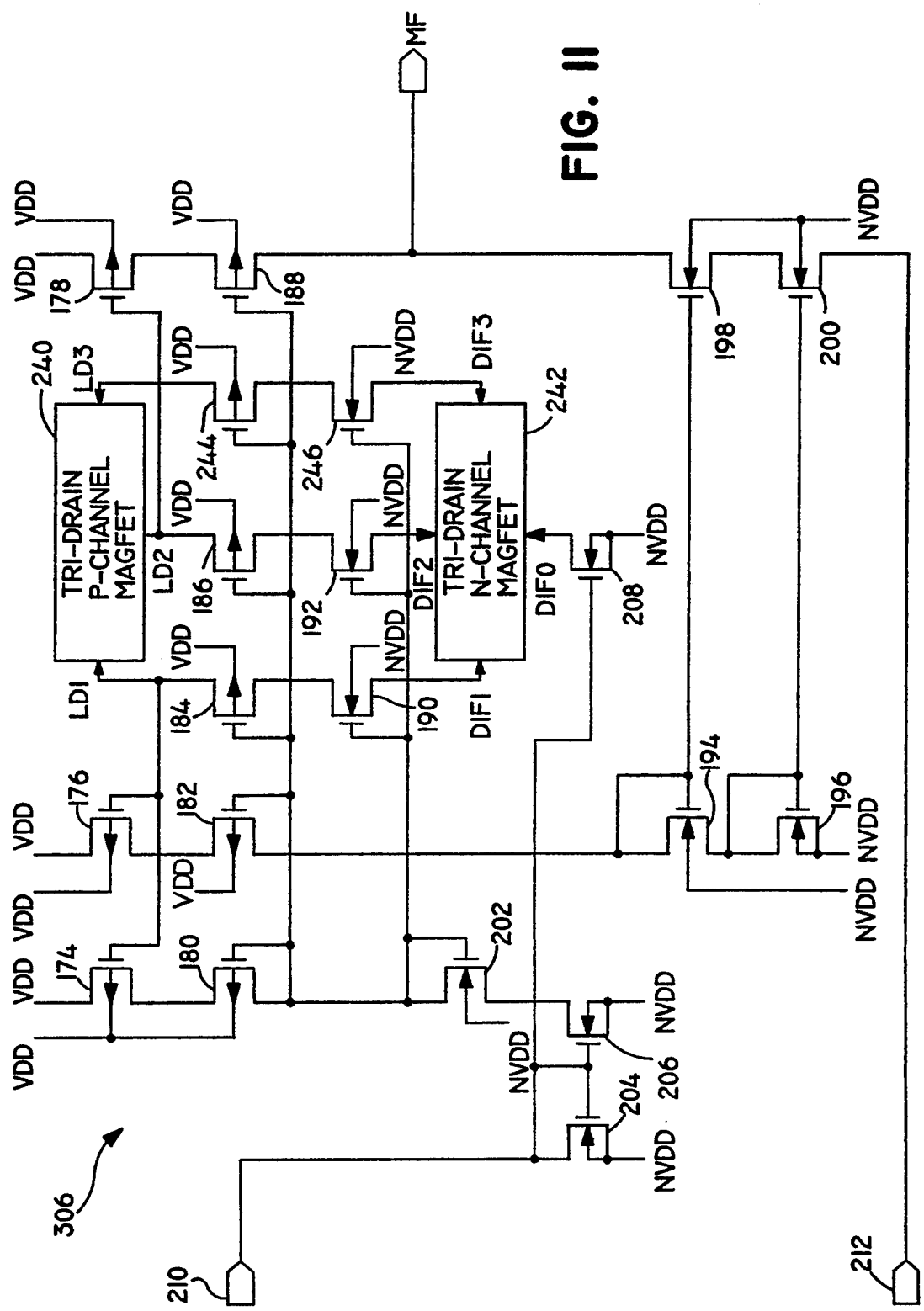
FIG. 11 is a schematic diagram of yet another alternative embodiment of a magnetic sensor circuit suitable for use in the pacemaker of FIG. 1.
Figure 12:
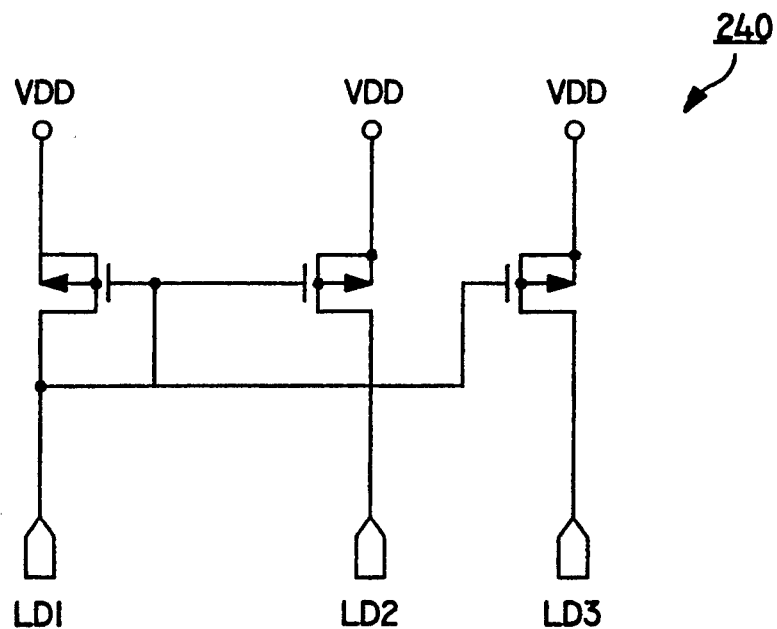
FIG. 12 is a schematic diagram of the P-channel MAGFET from the circuit of FIG. 11.
Figure 13:
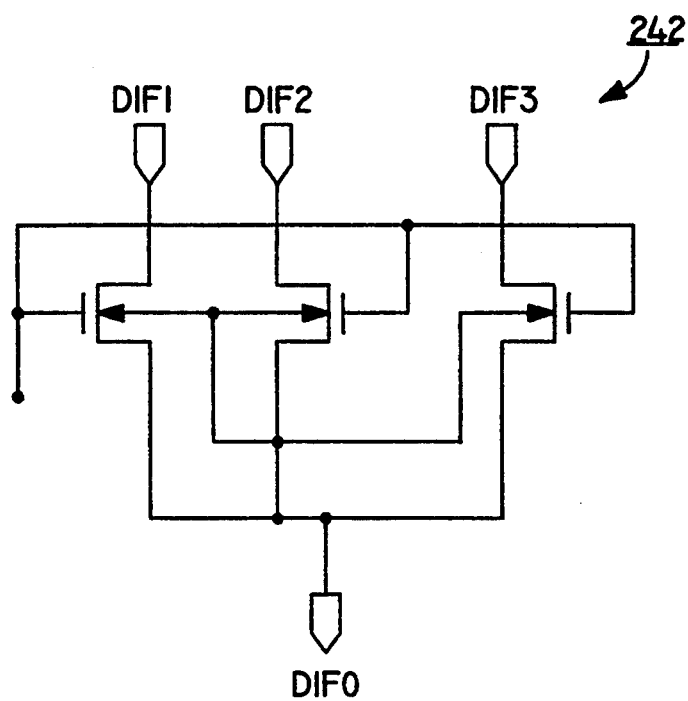
FIG. 13 is a schematic diagram of the N-channel MAGFET from the circuit of FIG. 11.

Another sensor 306 suitable for use in the implantable pacemaker 10 illustrated in FIG. 1 is shown in FIGS. 11, 12 and 13, wherein devices which are identical to corresponding devices in the embodiment of FIG. 6 have retained identical reference numerals. The embodiment of FIG. 11 employs a tri-drain MAGFET device 242 in place of the split-drain MAGFET 172 from FIG. 6. Active load device 240 and tri-drain MAGFET 242 are shown in greater detail in FIGS. 12 and 13, respectively. Active load device 240 is a 316μ/316μ tri-drain P-channel MAGFET. MAGFET 242 is a 316μ/316μ tri-drain N-channel MAGFET. The differential amplifier circuitry in the sensor 306 of FIG. 11 includes additional FET devices 244 and 246, having channel sizes of 38μ/4μ and 15μ/4μ situated between terminal LD3 of active load 240 and terminal DIF3 of tri-drain MAGFET 242.

Figure 14:
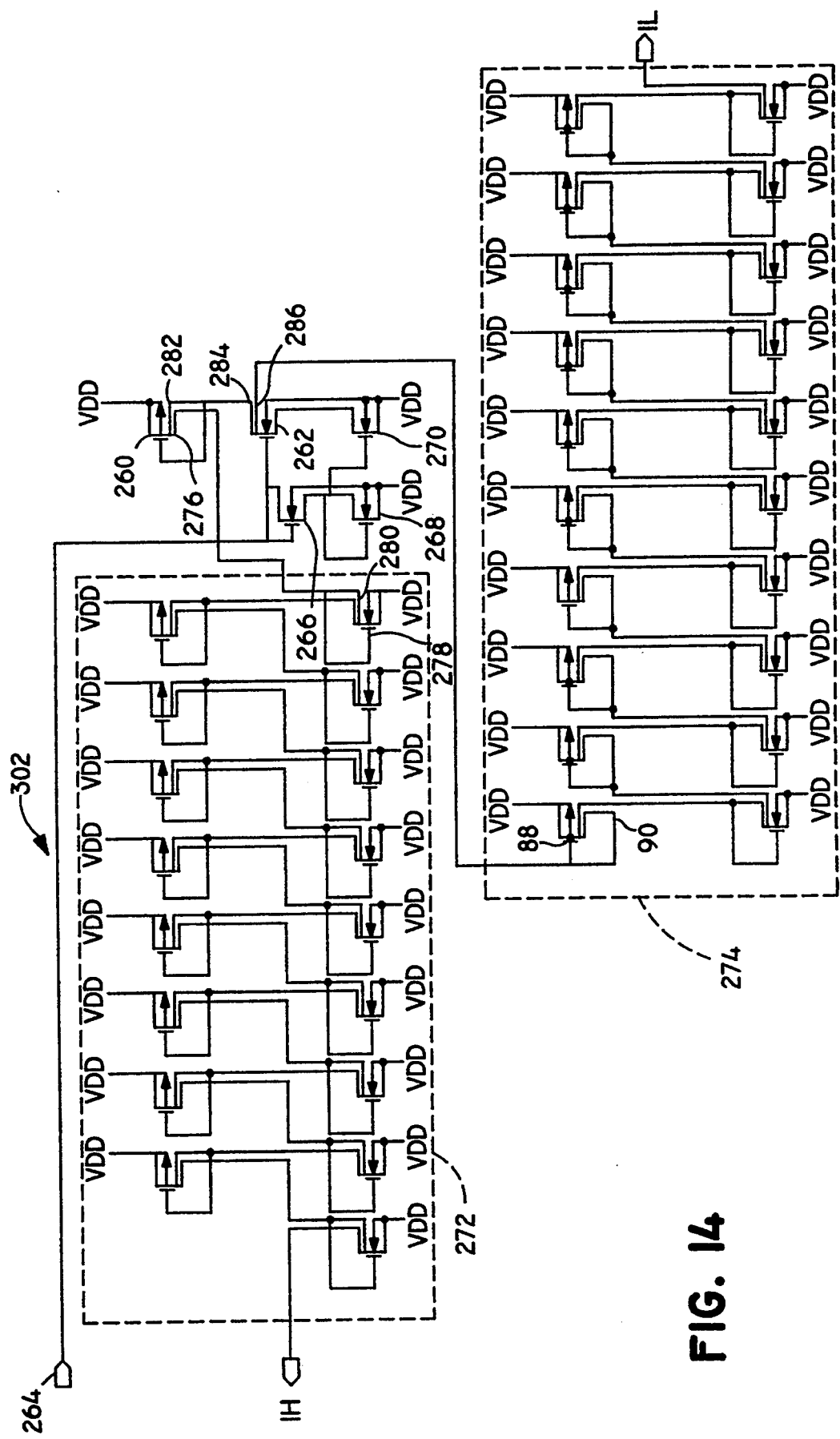
FIG. 14 is a schematic diagram of still another alternative embodiment of a magnetic sensor circuit suitable for use in the pacemaker of FIG. 1.

Still another magnetic sensor 302 suitable for use in the implantable pacemaker 10 illustrated in FIG. 1 is shown in FIG. 14. In the sensor 302 illustrated in FIG. 14, a plurality of split-drain MAGFETs are cascaded such that the current-crowding effects of an external magnetic field 128 are enhanced. In FIG. 14, a P-channel MAGFET 260 has one of its split-drain halves coupled to the split-drain half of an N-channel MAGFET 262. A 10 nano-amp current source is coupled to the sensor at terminal 264, this current source being regulated by conventional FET devices 266, 268, and 270. The MAGFETs in FIG. 14 are coupled such that current passing through MAGFET 260 is conducted serially through each of the "upper" MAGFETs designated collectively in FIG. 14 within dashed line 272, while current through MAGFET 262 is conducted serially through each of the "lower" MAGFETs designated collectively in FIG. 14 within dashed line 274. As shown in FIG. 14, split-drain half 276 of MAGFET 260 is coupled to the gate 278 of the first of the "upper" MAGFETs 272, as well as to one split-drain half 280 of that MAGFET. The second split-drain half 282 of MAGFET 260 is coupled to split-drain half 284 of MAGFET 262. The second split-drain half 286 of MAGFET 262 is coupled to the gate 288 and one split-drain half 290 of the first of the "lower" MAGFETs 274.

As would be apparent to one of ordinary skill in semiconductor design, when an external magnetic field 128 is applied to the sensor 302 of FIG. 14, the current-crowding effect described above in conjunction with FIG. 3 results in an increase in the current through split-drain half 276 of MAGFET 260, and a corresponding decrease in the current through split-drain half 286 of MAGFET 262. The intercoupling of the "upper" MAGFETs 272 causes the increased current in split-drain half 276 to be further increased as the current passes through each of the "upper" MAGFETs 272, since each of the MAGFETs 272 will experience the same current-crowding effects as MAGFET 260. Conversely, the decreased current in split-drain half 286 of MAGFET 262 will be further decreased as this current passes through each of the "lower" MAGFETs 274, which will also experience the current-crowding effects resulting from the external magnetic field. Thus, the current at terminal IH in FIG. 14 will be increased by an amount reflecting the increase in current through split-drain halves in each of the "upper" MAGFETs 272; current at terminal IL in FIG. 14 will be decreased by an amount reflecting the decrease in current through split-drain halves in each of the "lower" MAGFETs 274. The resulting differential between the currents at IH and IL will thus reflect the additive effects of current crowding through each of the "upper" MAGFETs 272 and "lower" MAGFETs 274.

Figure 15:
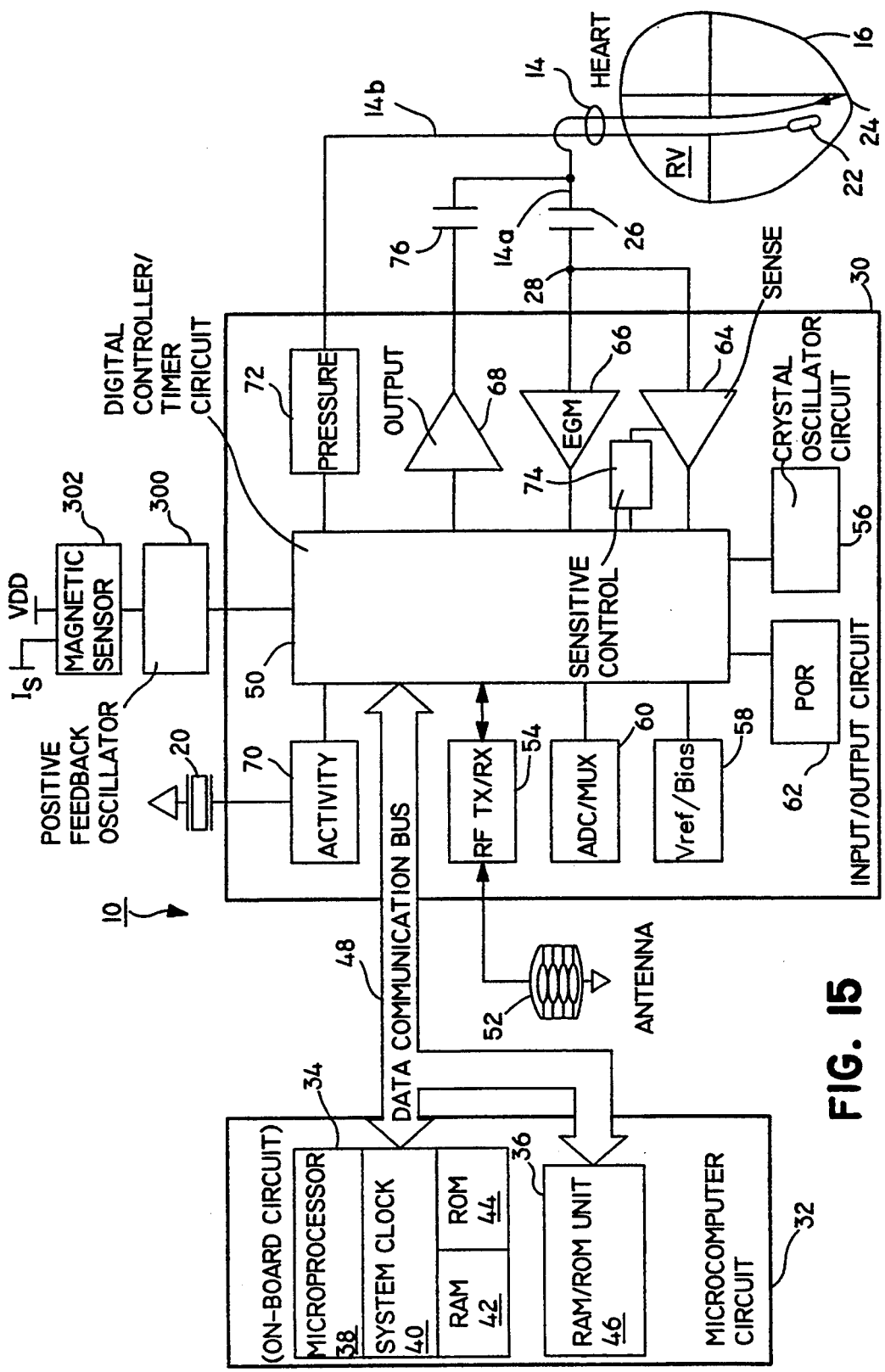
FIG. 15 is a block diagram of the circuitry of the pacemaker of FIG. 1 using the magnetic sensor of FIG. 14 in conjunction with a positive feedback oscillator.

It is contemplated by the inventors that the current differential between IH and IL resulting from application of an external magnetic field 128 to the sensor 302 of FIG. 14 can be utilized to control the duty cycle of a positive-feedback oscillator 300 illustrated in FIG. 15, well known in the art of circuit design. In this way, the application of a magnetic field 128.can be indicated by a change in the duty cycle of the oscillator 300. It is anticipated that the change in the average voltage of the duty cycle modulated signal from oscillator 300 would be obtained by low-pass filtering of the signal. No trim would be required in this embodiment.

Moving now to FIG. 15, there is illustrated an implantable pacemaker circuit suitable for use in the pacemaker 10 illustrated in FIG. 1. This embodiment of the implantable pacemaker 10 uses the magnetic sensor 302 illustrated in FIG. 14 to drive a positive feedback oscillator 300 and control its duty cycle. The output of oscillator 300 which is sent to digital controller/timer 50, is a filtered signal representative of the application of a magnetic field.

Figure 16:
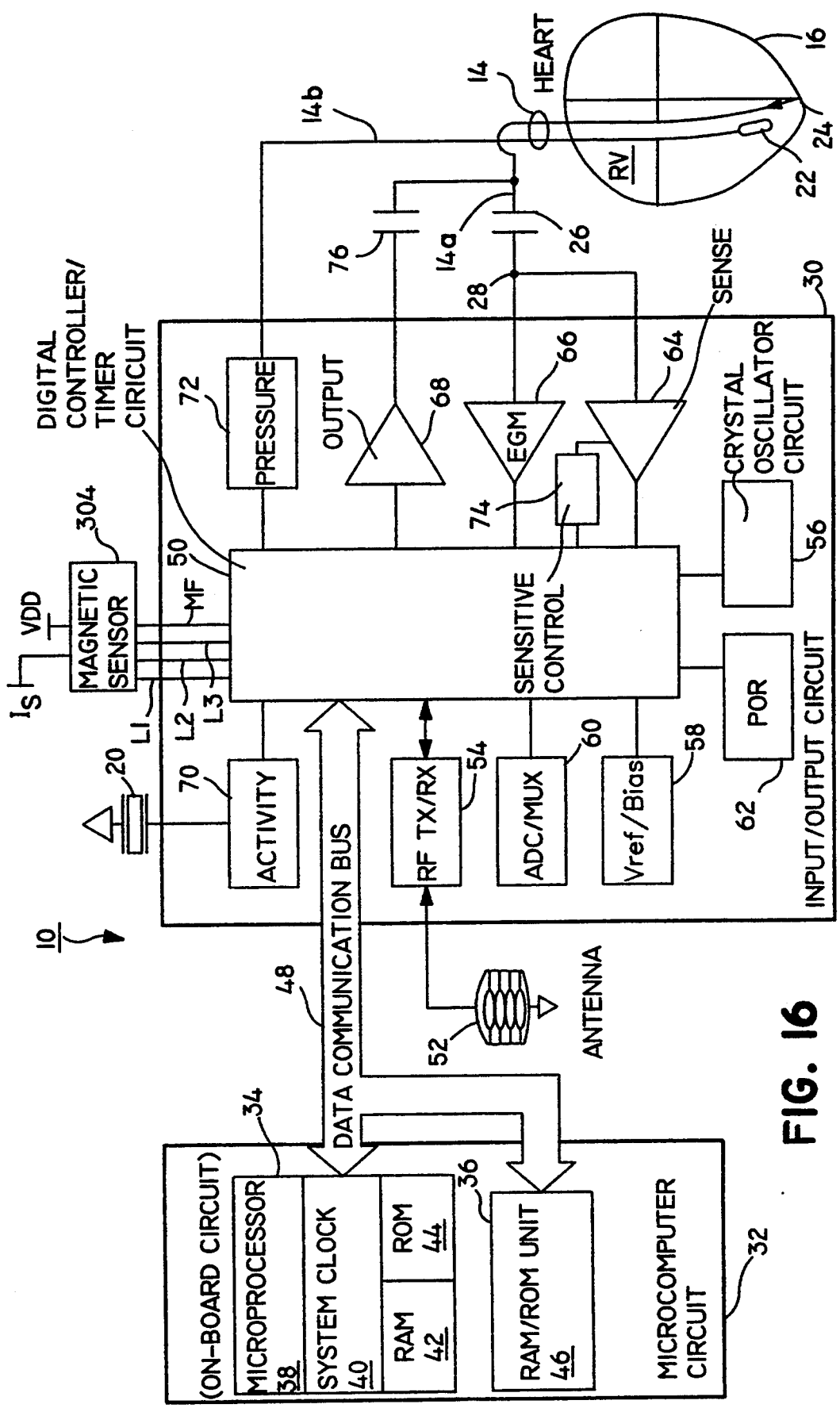
FIG. 16 is a block diagram of the circuitry of the pacemaker of FIG. 1 using the magnetic sensor of FIG. 9 having a multiplexed input for altering the sensing characteristics of the magnetic sensor.

FIG. 16 illustrates yet another embodiment of the present invention wherein the magnetic sensor 304 illustrated in FIG. 9 is used in the implantable pacemaker 10 illustrated in FIG. 1. In this embodiment, magnetic sensor 304 has an internal multiplexer 220 connected to digital controller/timer 50. Controller/timer 50 selects any one of sensor 304 lines L1, L2 or L3 which causes the output of sensor 304 to change respectively in response to the introduction of a magnetic field 128 as hereinbefore described.

In each of the embodiments of the present invention disclosed herein, it is contemplated that the MAGFET sensor utilized may be implemented as a separate component of an implantable medical device, such as an implantable pacemaker, cardioverter, defibrillator, neural stimulator, or the like, in order that the MAGFET sensor may be substituted for the reed switch in .existing designs. Alternatively, the MAGFET sensor may be implemented in new designs as an integral part of the CMOS integrated circuit typically included in such devices. In either case, certain constraints exist with respect to the packaging of the MAGFET sensors and placement of the MAGFET sensor within the implantable device's enclosure.

Although CMOS integrated circuits are commonly packaged in Kovar-covered ceramic leadless chip carriers, such an arrangement may not be suitable for circuits which incorporate a MAGFET sensor in accordance with the present invention, as such packaging may tend to interfere with or deflect an externally applied magnetic field. In addition, circuits containing MAGFET sensors in accordance with the present invention must be positioned within an implanted device away from other ferromagnetic materials which may also be contained therein.

From the foregoing description of specific embodiments of the present invention, it should be apparent that a solid-state magnetic sensor has been disclosed which due to its operability at low bias currents and supply voltages is particularly well-suited for use in an implantable medical device. While specific embodiments of the present invention have been disclosed in detail, it is to be understood that various alterations, modifications, or substitutions therein may be made without departing from the spirit and scope of the present invention, as defined in the claims, which follow.

What is claimed is:

1. A magnetic field sensor for sensing the presence of a magnetic field comprising:
    (a) a voltage source;
    (b) a current source;
    (c) a first split-drain FET having a source and first and second split-drain halves;
    (d) a second split-drain FET having a source and third and fourth split-drain halves, wherein said first split-drain half is coupled to said fourth split-drain half, wherein said source of said first split-drain FET is coupled to said voltage source and said source of said second split-drain FET is coupled to said current source to allow current to be conducted from said voltage source through said first and fourth drain halves to said current source; and
    output means coupled to said first and second split-drain FET's for producing an output signal in response to a magnetic field applied to said first and second split-drain FET's.

2. A sensor according to claim 1, wherein:
    said second split-drain half is coupled to said third split-drain half to allow current to be conducted from said voltage source through said first, second, third, and fourth split-drain halves to said current source, wherein a first portion of said current is conducted through said first split-drain half and said fourth split-drain half, and a second portion of said current is conducted through said second split-drain half and said third split-drain half and wherein application of a magnetic field increases one of said first and second portions of said current and decreases the other of said first and second portions of said current.

3. A sensor according to claim 2, wherein said output means comprises means for producing said output signal responsive to relative magnitudes of said first and second portions of said current.

4. A sensor according to claim 3, wherein said output means comprises amplifier means for generating said output signal.

5. A sensor according to claim 1, wherein said first split-drain FET is a P-channel split-drain FET, and wherein said second split-drain FET is an N-channel FET.

6. A sensor according to claim 1 or claim 2 or claim 5 wherein said first and second split-drain FET's are tri-drain FET's.

7. A sensor according to claim 1 or claim 5, further comprising a third split drain FET having a source and fifth and sixth split drain halves, means for coupling said source of said third split-drain FET to said voltage source and means for selectively coupling to either said first split drain half or said fifth split drain half to said fourth split drain half.

8. A sensor according to claim 7 further comprising means for selectively coupling either said sixth split drain half or said second split drain half to said third split drain half.

9. A sensor according to claim 1 or claim 5, wherein said sensor further comprises:
- a current drain;
- a third split-drain FET coupled to said second split-drain half and said current drain;
- a fourth split-drain FET coupled to said third split-drain half and said current drain; and
- wherein said output means comprises oscillating means coupled to said third and fourth split-drain FET's, for producing an output signal which varies as a function of relative current flow through said third and fourth split drain FET's.

10. A sensor according to claim 1 or claim 5, wherein said sensor further comprises:
- a current drain;
- a first plurality of split-drain FET's coupled to said second split-drain half and said current drain;
- a second plurality of split-drain FET's coupled to said third split-drain half and said current drain; and
- wherein said output means comprises oscillator means coupled to said first and second plurality of split-drain FET's, for producing an output signal which varies as a function of relative current flow through said first and second pluralities of split drain FET's.

11. A sensor according to claim 1 or claim 2 or claim 5, wherein said output means comprises means for producing an output signal indicative of the direction of said magnetic field.

* * * * *